Figure 1:
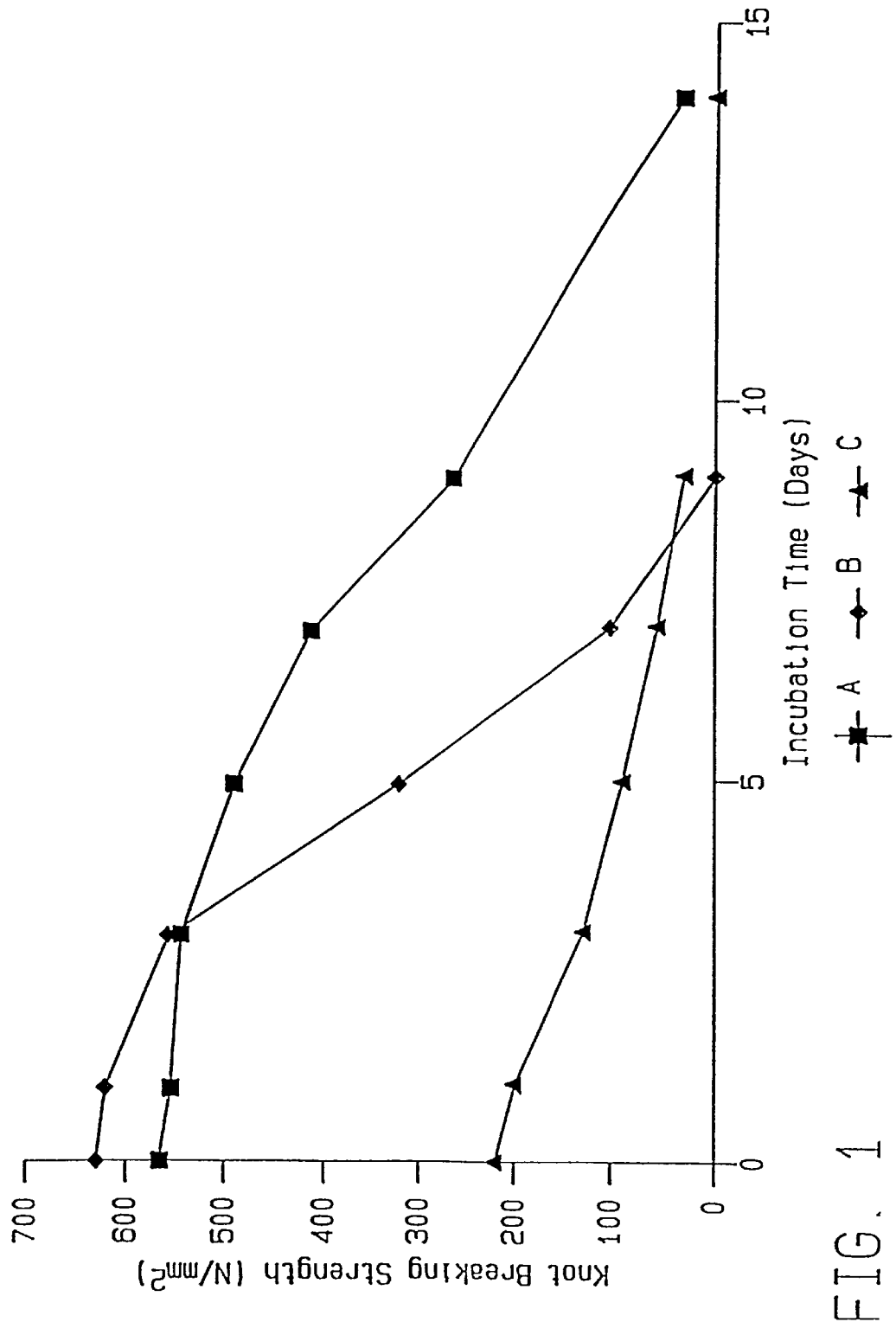

United States Patent [19]
Goldmann et al.

[11] Patent Number: 6,011,121
[45] Date of Patent: *Jan. 4, 2000

[54] SURGICAL SUTURE MATERIAL, ITS USE IN SURGERY AND PROCESS FOR ITS PRODUCTION

[75] Inventors: Helmut Goldmann, Melsungen; Helmut Hierlemann, Goeppingen; Erhard Mueller, Stuttgart; Heinrich Planck, Nuertingen, all of Germany

[73] Assignee: B. Braun Surgical GmbH, Melsungen, Germany

[ * ] Notice: This patent is subject to a terminal disclaimer.

[21] Appl. No.: 08/910,715

[22] Filed: Aug. 13, 1997

Related U.S. Application Data

[62] Division of application No. 08/555,818, Nov. 9, 1995, Pat. No. 5,695,879.

[30] Foreign Application Priority Data

Nov. 10, 1994 [DE] Germany ............................ 44 40 095

[51] Int. Cl.⁷ .............................. C08G 63/91; C08G 63/68
[52] U.S. Cl. ........................ 525/415; 528/354; 428/364; 264/176.1
[58] Field of Search ........................... 525/415; 528/354; 428/364; 264/176.1

[56] References Cited

U.S. PATENT DOCUMENTS

| | | | |
|---|---|---|---|
| 3,736,646 | 6/1973 | Schmitt et al. | 29/458 |
| 3,867,190 | 2/1975 | Schmitt et al. | 117/138.8 |
| 3,945,052 | 3/1976 | Liebig | 3/1 |
| 4,033,938 | 7/1977 | Augurt et al. | 260/78.3 R |
| 4,047,252 | 9/1977 | Liebig et al. | 3/1.4 |
| 4,243,775 | 1/1981 | Rosensaft et al. | 525/415 |
| 4,300,565 | 11/1981 | Rosensaft et al. | 128/335.5 |
| 4,441,215 | 4/1984 | Kaster | 128/334 |
| 4,441,496 | 4/1984 | Shalaby et al. | 128/335.5 |
| 4,653,497 | 3/1987 | Bezwada et al. | 128/335.5 |
| 4,700,704 | 10/1987 | Jamiolkowski et al. | 128/335.5 |
| 4,705,820 | 11/1987 | Wang et al. | 524/381 |
| 5,320,624 | 6/1994 | Kaplan et al. | 606/77 |
| 5,468,253 | 11/1995 | Bezwada et al. | 606/230 |
| 5,695,879 | 12/1997 | Goldmann et al. | |

FOREIGN PATENT DOCUMENTS

| | | |
|---|---|---|
| 872208 | 5/1979 | Belgium . |
| 098 394 | 1/1984 | Canada . |
| 210 9451 | 5/1994 | Canada . |
| 0 108 171 | 10/1982 | European Pat. Off. . |
| 0 391 586 | 3/1990 | European Pat. Off. . |
| 0 608 139 | 7/1994 | European Pat. Off. . |
| 2 334 488 | 4/1976 | France . |
| 24242 | 11/1962 | Germany . |
| 2 255 743 | 11/1972 | Germany . |
| 2 206 144 | 8/1973 | Germany . |
| 24 61 370 | 12/1974 | Germany . |
| 25 01 448 | 7/1975 | Germany . |
| 160 857 | 4/1984 | Germany . |
| 39 37 272 | 5/1991 | Germany . |
| 2 033 411 | 5/1980 | United Kingdom . |
| 8 201 647 | 5/1982 | WIPO . |

OTHER PUBLICATIONS

P.F. Nockemann, "Suture Materials–General Part", Surgical Suture, 3.ed. (1980) p. 42.
Ray et al., "Polydioxanone (PDS), A novel Monofilament Synthetic Absorable Suture", Surgery, Gynecology & Obstetrics (1980) vol. 153.
Katz et al., A new Synthetic Monofilament Absorable Suture Made From Polytrimethylene Carbonate, Surgery, Gynecology & Obstetrics (1985 (vol. 161)) .
Biomaterials, vol. 16; "Monocryl suture, a new ultra–pilable Absorable mono filament suture" Bezwada, et al., B. 1141–1148, 1995.
Biomaterial, vol. II; "Invivo and in vitro degradation of momofilament absorable sutures PCS and Manko", Metz, et al. pp. 41–45, Jan. 1990.

*Primary Examiner*—William Krynski
*Assistant Examiner*—J. M. Gray
*Attorney, Agent, or Firm*—Pennie & Edmonds LLP

[57] ABSTRACT

A surgical suture material of absorbable, synthetic polymer is formed from glycolide-trimethylene carbonate copolymer with a glycolide content higher than 76 wt. % and with a statistical distribution of the monomers. Within 9 to 21 days, the suture material has a complete breaking strength loss and is completely absorbed in vivo after 35 to 91 days.

9 Claims, 2 Drawing Sheets

SURGICAL SUTURE MATERIAL, ITS USE IN SURGERY AND PROCESS FOR ITS PRODUCTION

This is a division, of application Ser. No. 08/555,818, filed Nov. 9, 1995 now U.S. Pat. No. 5,695,879.

The present invention relates to surgical suture material made from absorbable, synthetic polymer, its use in surgery and process for its production.

Surgical suture material usable for wound closure comprises non-absorbable and absorbable materials. Absorbable surgical sewing threads based on natural biological materials, particularly cat gut and absorbable synthetic sewing threads are known. Absorbable synthetic suture material can inter alia be produced from polyglycolic acid (PGA). In the physiological environment the sewing threads undergo a hydrolysis. The 50% breaking strength loss, also known as the half-life period, serves as a measure for the hydrolytic decomposition of the polymer material. Surgical sewing threads formed from braided PGA multifilaments (e.g. obtainable under the trademark Dexon) within 21 days have a 50% breaking strength loss and an absorption of hydrolyzates within 100 to 120 days. A multifilament sewing thread produced from a glycolide-lactide copolymer with a comonomer ratio of 90:10 has similar characteristics (obtainable under the trademark Vicryl). In vivo, after 25 days it loses 50% of its initial strength and is absorbed after more than 80 days.

Hitherto known absorbable synthetic suture material in the form of multifilament sewing threads suffers from a number of disadvantages, such as e.g. poor fabric passage, sawing action or capillarity. Monofilaments made from the described polymers have a high stiffness and a poor knotting behavior, which is disadvantageous for the use thereof as surgical suture material.

Monofilament sewing threads based on polyglycolic acid are also known, which contain softening components in the PGA matrix. From a copolymer of glycolide and trimethylene carbonate in a ratio of 68:32 (available under the trademark Maxon), it is possible to produce a surgical monofilament thread, whereof up to 50% of the initial strength is maintained for more than about 5 weeks and which is completely absorbed after about 7 months. Flexible, usable monofilaments can also be extruded from polydioxanone (available under the trademark PDS). The breaking strength loss and absorption time are comparable with glycolide/trimethylene carbonate (trademark Maxon) threads (cf. following table).

| Polymer | Trade name | Thread | 50% breaking strength loss (weeks) | Resorption time (months) |
|---|---|---|---|---|
| Polyglycolic acid | Dexon$^R$ | braided | 3* | 3–4* |
| Glycolide/lactide copolymer (90:10) | Vicryl$^R$ | braided | 3–4* | 3* |
| Glycolide/TMC copolymer (68:32) | Maxon$^R$ | monofilament | 5** | 7** |
| Polydioxanone | PDS$^R$ | monofilament | 5*** | 6*** |

*P. F. Nockermann: Die chirurgische Naht, Georg Thieme Verlag Stuttgart, 3rd edition, p 42
**A. R. Katz, D. P. Mukberjec, A. L. Kaganov and S. Gordon in: Surg. Gynecol. Obstet. 161, 213 (1985)
***J. A. Ray, N. Doddi, D. Regula, J. A. Williams and A. Melveger in: Surg. Gynecol. Obstet. 153, 497 (1981)

However, these monofilament threads have a very slow decomposition behavior in living tissue and are only completely absorbed by the body after several months. Their absorption time is twice as long as known filament threads. Thus, more recent developments cover monofilament sewing threads made from absorbable polymers with shorter half-life periods and faster absorption.

U.S. Pat. No. 4,653,497 describes the two-stage production of crystalline copolymers from 1,4-dioxanone and glycolide, as well as the characteristics of the monofilament threads produced therefrom. After 4 weeks in vivo, said monofilaments still have 10 to 30% of their initial strength and are absorbed after about 4 to 5 months.

U.S. Pat. No. 4,700,704 claims copolymers of glycolide and ε-caprolactone and the monofilaments produced therefrom. These surgical, monofilament sewing threads, after 7 days implantation, have 44 to 62% of their strength and after 14 days 11 to 37% thereof.

According to U.S. Pat. No. 4,441,496 it is possible to process to monofilaments copolymers comprising 1,4-dioxanone and 2,5-morphalinodiones which, after 28 days, have up to 50% of the initial strength and which are completely absorbed after 90 to 180 days.

DE-OS 2206144 discloses copolymers of glycolide as the main component and other cyclic comonomers such as e.g. ethylene carbonate and trimethylene carbonate. With an ethylene carbonate proportion of 15 to 25%, the absorption time is 30 to 60 days (with 15%) or 15 to 30 days with a higher ethylene carbonate content.

U.S. Pat. No. 4,243,775 and U.S. Pat. No. 4,300,565 describe the successive polymerization of glycolide and trimethylene carbonate leading to block polymers. The monofilament threads produced from this sequential copolymer have in the case of a trimethylene carbonate content of 15 wt. %, after 21 days in vivo, a linear breaking strength of 45% of the initial value and with a weight proportion of 45% have a linear breaking strength of 38% after 21 days.

GB-A-2033411 also claims sequential copolymers of glycolide and trimethylene carbonate (TMC), with a preferred TMC content of 10 to 20%. The residual strength of extruded monofilaments is 45% 21 days after implantation.

In certain areas of surgical wound closure long absorption times and a long maintenance of the breaking strength are unnecessary, because the tissue rapidly recovers its strength and consequently the thread loses its function. Examples of such indications are intestinal sutures, sutures in the vicinity of the mucous membranes of the tooth-mouth-jaw area and gynecological applications. In the case of surgical sewing threads for such applications an accelerated hydrolytic decomposition and consequently a faster absorption are desired. It is sufficient if there is an adequate suture strength for a few days. A good knot breaking strength and good knottability are consequently necessary for a reliable, safe use. At present, for such indications, there are only synthetic material multifilament sewing threads, which suffer from the disadvantages referred to hereinbefore.

The problem therefore arises of making available a surgical suture material of absorbable synthetic polymer in the form of a monofilament having an accelerated decomposition behavior and improved absorption, which overcomes the disadvantages of the known suture materials, is easy and inexpensive to manufacture, as well as easy and reliable to use.

This problem is solved by a surgical suture material of absorbable synthetic polymer, which is characterized in that it is formed from glycolidetrimethylene carbonate copolymer with a glycolide content above 76 wt. % with a statistical distribution of the monomers. A copolymer having a statistical distribution of monomer units is known in the art as a random copolymer. Preferably, the suture material according to the invention is in the form of a monofilament with a diameter of 0.001 to 0.8 mm. In such a material according to the invention the glycolide content, based on the total copolymer is preferably more than 78 wt. %. Based on the total copolymer, its glycolide content can in particular be 80 to 99 wt. %. In a preferred embodiment of the invention its glycolide content can be 83 to 93 wt. %, based on the total copolymer.

It has surprisingly been found that monofilaments can be produced from statistical copolymers of glycolide and trimethylene carbonate (TMC) with a glycolide content of more than 76 wt. %, which have the very good characteristics necessary for a surgical suture material, particularly with respect to the physical characteristics and practical handling, and which are much more rapidly degraded and absorbed than the prior art monofilaments formed from the same comonomers, which are sequentially polymerized, i.e. reacted to block copolymers.

Suture material of statistical copolymer according to the invention is advantageously characterized by an accelerated absorbability in living tissue. Preferably, its absorbability is less than 100 days. In particular, its absorption time is in vivo 35 to 91 days. Preferably its absorption time in vivo is 42 to 56 days.

The decomposition of the polymer according to the invention takes place in the body of an animal or human by metabolic processes. Body and tissue fluids participate in the reaction. Through hydrolysis the polymer chain is split into smaller and more readily soluble fragments. The fragments are further decomposed, optionally accompanied by the participation of enzymatic processes. The decomposition products are transported away by the metabolic system and are expelled from the organism in the same way as other metabolic waste. It is important for good compatibility of the absorbable suture material with the patient, that during the decomposition process no harmful metabolites can be formed or concentrated. Polyglycolic acid is in particular characterized in that during its decomposition in vivo no toxic decomposition products are formed. The trimethylene carbonate used as a comonomer according to the invention is also characterized by good compatibility and the avoidance of toxic reactions.

The statistical glycolide-TMC copolymer according to the invention differs from the conventional, sequential glycolide-TMC copolymers hitherto used for producing surgical suture material through the modified sequence of the monomer units in the macromolecule chain. This also influences the interactions between the individual chain molecules in an already formed filament. As is known to the experts in the field of fibre technology, the physical and mechanical properties of a fibre are dependent on the orientation and structure of the chain molecules, particularly the formation of amorphous and crystalline regions. As has been revealed by analyses of the microstructure, the inventive suture material of statistical glycolide-TMC copolymer can have a crystallinity of 15 to 40%. It is also characterized by an inherent viscosity (limit viscosity) of 1.0 to 2.0 dl/g, particularly 1. to 1.6 dl/g, measured in 0.1% hexafluoroisopropanol (HFIP) at 30° C.

The material according to the invention has advantageous mechanical characteristics. Thus, the monofilament suture material according to the invention can have a tensile strength of 250 to 900 N/mm$^2$, particularly 300 to 650 N/mm$^2$. These tensile strength values correspond to those for recognized, readily absorbable, surgical sewing threads according to the prior art and which are required by pharmacopoeias, or even significantly exceed these values. The surgical suture material according to the invention can have an elongation at break of 25 to 45%, particularly 30 to 40%. Thus, the monofilament according to the invention is particularly suitable for surgical applications.

The decomposition of polymer chains during absorption is linked with a reduction in the mechanical strength of the filament material. After 3 to 10 days, particularly 4 to 6 days, the surgical suture material according to the invention can still have 50% of its tensile strength. The degradation of the suture material means that, in vivo, within 7 to 28 days it can have a complete breaking strength loss. In particular, a material according to the invention, in vivo, within 9 to 21 days can have a complete breaking strength loss.

Investigations of the behavior of the mechanical characteristics over a period of time and therefore the decomposition behavior of the suture material according to the invention reveals significant differences compared with the behavior of known, absorbable, surgical suture materials. The investigations are described in greater detail in the following examples and in the accompanying drawings. As has been mentioned hereinbefore, surgical suture materials formed from statistical glycolide-TMC copolymers according to the invention have a higher initial strength than known, resorbable, multifilament materials. Filaments from from 84 wt. % glycolide and 16 wt. % trimethylene carbonate can give good results. Both in vitro and in vivo tests have revealed that the strengths of the samples according to the invention only decrease slowly during the first 3 days and remain above the values of the known multifilament materials. Subsequently there is an accelerated reduction of strength. This decomposition behavior is particularly pronounced in the case of the glycolide-TMC copolymer with a monomer ratio of 92:8.

Advantageously the surgical suture material of absorbable, synthetic polymer is in the form of a monofilament of glycolide-trimethylene carbonate copolymer with a statistical distribution of the monomers and is suitable for use for wound closure with accelerated absorption. The aforementioned advantageous, mechanical characteristics of monofilament sewing threads of statistical glycolid-TMC copolymer permit a simple handling of the suture material during the sewing of tissue in an animal or human body, e.g. when fixing organs, closing tears in the body tissue or closing surgical incisions. In particular as a result of the construction of a monofilament with a smoother thread surface than a multifilament sewing thread, the tissue to be treated can be protected against damage during suture application. This limits the risk of side-effects for the patient, such as e.g. delayed healing and tissue granuloma formation. The good knottability and knot strength in conjunction with the high initial tensile strength and extensibility permit a reliable fixing and stabilization of the joined wound edges during the first days following surgery. In particular, during said first days, regenerative, endogenic tissue can be used in reliable manner for natural wound healing, because the risk of a tearing apart of the wound edges during movement of the patient is reduced by the secure fixing.

A process for the production of surgical suture material of absorbable synthetic polymer is characterized in that glycolide and trimethylene carbonate monomers are simultaneously reacted to a statistical copolymer. The monomers can be 1,4-dioxan-2,5-dione and 1,3-dioxan-2-one in proportions necessary for the desired copolymer. To the monomer mixture can be added a suitable catalyst, e.g. tin octoate, in the quantity normally required. The reaction is carried out as a melt polymerization in a suitable reactor, which is heatable and provided with a stirrer. The polymerization reactor must in particular be designed in such a way that the highly viscous melts obtained are homogenized, the necessary temperature ranges maintained and the raw polymer can be substantially completely removed from the reactor. Reactors of this type are inter alia offered for sale by Werner & Pfleiderer, Stuttgart, AMK in Aachen or Haake in Karlsruhe.

The copolymerization reaction can be performed in accordance with conventional, known procedures for the production of statistical copolymers. Preferably the reaction mixture is heated accompanied by constant thorough mixing, particularly at a temperature of 170 to 190° C. and preferably 175 to 185° C. During a reaction of 30 to 100 minutes, the monomers can be reacted to a statistical copolymer.

At the end of the reaction the raw copolymer is heated for a short time beyond the reaction temperature and discharged as a melt and after cooling is granulated in the usual way. By extraction, e.g. with ethyl acetate or some other suitable solvent, low molecular weight fractions and residual monomers can be separated. The resulting polymer granules are then dried. Drying can take place according to conventional processes, particularly at elevated temperature and/or under reduced pressure. Any extractant residues still adhering to the raw copolymer can be removed by evaporation during drying. In the same way monomer residues can be optionally eliminated during drying. Optionally a further purification stage can be performed for obtaining a high-purity copolymer according to the invention. Preferably such a purification takes place before the drying stage.

The statistical glycolide-TMC copolymer with a composition ratio according to the invention is characterized by a melting range of 170 to 215° C. This melting range can be at higher temperatures, particularly with a higher glycolide proportion. The glycolide-TMC copolymers produced according to the invention are also characterized by a melting enthalpy in the range 40 to 65 J/g. In the case of copolymers with a higher glycolide proportion, the melting enthalpy can be in a higher value range.

The copolymer according to the invention has a partially crystalline structure. This results from the high glycolide content of more than 76 wt. %. Due to the high glycolide content the polymer material has increased stiffness which affects its properties in the use as suture material in practice. Advantageously the suture material can include a plasticizer. The plasticizer can be present in an amount of 1–25 wt. %, based on the total weight of the copolymer and plasticizer, in the suture material. The plasticizer is characterized in that it is physically dissolved in the copolymer. The plasticizer is biocompatible and/or biodegradable. Advantageously, glyceryl triacetate, butyl citrate, triethyl citrate, or acetyltributyl citrate can be used for glycolide-TMc copolymers according to the invention. Preferably can be used oligomers of $\epsilon$-caprolactone as plasticizers. Further also oligomers of TMC are appropriate as plasticizers in the copolymer according to the invention. Advantageously the oligomers to be used according to the invention have a maximum molecular weight of 22000, particularly of 20000, which corresponds to about 400 units of caprolactone. Preferably the plasticizer has a viscosity in the range of viscous flowing to solid. The intrinsic viscosity at 25° C. is particularly in the range of 0.05 to 0.5 dl/g. As to the interrelation of viscosity and molecular weight of polymers see Schindler, A. et al. in: Journ. Polym. Sci., Vol. 20, p. 319–326 (1982), and Rafler, E. in: Acta Polym. 44, p. 168–170 (1993). Admixing of the plasticizer to the copolymer can be done with the molten polymer or in solution. The amount of plasticizer added can be about inversely proportional to the amount of TMC in the copolymer. The TMC in the copolymer acts as a so-called internal plasticizer. An additionally included plasticizer acts as a so-called external plasticizer. The copolymer with a plasticizer content according to the invention does not exhibit elastomeric properties.

Surgical suture material can be produced by known processes from the polymer material produced according to the invention. In particular, the statistical glycolide-TMC copolymer according to the invention can be spun to monofilaments in a melt spinning process. For example, the polymer material according to the invention, can be heated to its melting point in a conventional extruder installation, e.g. a single-screw extruder and extruded through suitable spinnerets to monofilaments. In a preferred embodiment, dried glycolide-TMC copolymer can be melted at a temperature in the range 170 to 235° C. For extrusion purposes, use is preferably made of a spinneret with a diameter of 0.5 to 1.5 mm. Advantageously the filament formed is extruded in a cooling bath, preferably water at ambient temperature.

In order to obtain the requisite mechanical properties, the extruded filament can be stretched or drawn for orienting the molecule chains. Advantageously it is stretched or drawn with a stretch or draw ratio of 1:4 to 1:10. In order to ensure that the orientation, mechanical properties and dimensional stability of the filaments are permanently maintained, the stretched polymer material can be fixed. Fixing takes place at temperatures between ambient temperature and 95° C., preferably between 40 and 80° C. It is particularly preferred that stretching and fixing take place immediately following extrusion, more especially in a combined process. Advantageously use is made of an apparatus constituted by combined, appropriate means.

The diameter of the monofilaments produced in this way is in the standard range 0.001 to 0.8 mm. Advantageously, the monofilaments according to the invention are characterized by the aforementioned mechanical characteristics.

Glycolide-TMC copolymer filaments produced according to the invention can be processed to surgical suture material by conventional methods, e.g. cut to suitable lengths. In particular the polymer material according to the invention can be appropriately sterilized. An appropriate sterilization process can be chosen from among standard physical or chemical methods for deactivating microorganisms or a combination of such methods. Preferably, the suture material according to the invention is sterilized using ethylene oxide.

Advantageously the surgical suture material, cut to appropriate lengths is appropriately packed ready for use. In a preferred embodiment the sewing threads according to the invention can be provided with surgical needles.

Due to the hydrolytic decomposability of the polymer material according to the invention, the suture materials must be protected from moisture and elevated temperatures during storage, so that the strength characteristics are fully maintained up to the time of use. Advantageously the surgical suture materials according to the invention are dried in the ready for use state and appropriately packed. This appropriately takes place in a pack protected against moisture intrusion and in particular in moisture-proof film material, more especially a vacuum pack. In addition, a dry, cool storage location should be chosen.

According to a particularly preferred embodiment surgical suture threads of glycolide-TMC copolymer can be cut to length ready for use, provided with surgical needles and sterilized and placed in a sterile pack protected against moisture and suitable for simple removal.

Further features and details of the invention can be gathered from the following exemplified description of preferred embodiments. The individual features can be implemented individually or in subcombinations. Reference is also made to the attached drawings, wherein show:

FIG. 1 The change to the tensile strengths in vitro over an incubation time of 14 days of two suture materials according to the invention and a comparison, prior art material.

Figure 2:
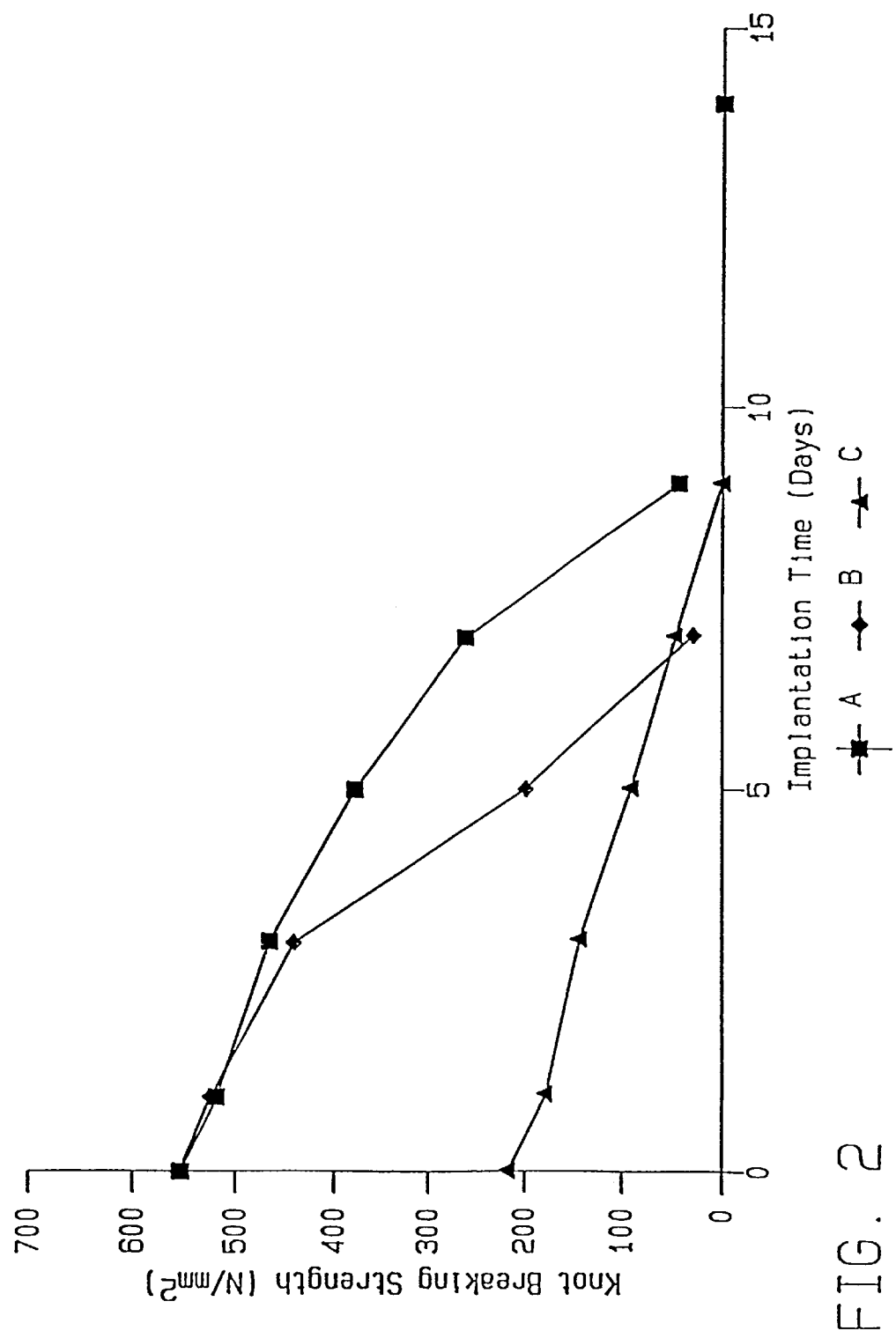

FIG. 2 The change to the tensile strengths in vivo over an implantation time of 10 days of two suture materials according to the invention and a comparison, prior art material.

The examples merely serve to illustrate the invention, which is in no way limited thereto.

EXAMPLE 1

Production of glycolide-TMC copolymer with a monomer ratio of 76:24.

Polymerization takes placein a Helicone-2 CV reactor with a usable volume of approximately 200 ml. For the synthesis of the statistical copolymer 146 g of glycolide and 54 g of trimethylene carbonate are weighed in under inert conditions and mixed with 80 ppm of tin (as tin octoate in a toluene solution). After removing the toluene in a high vacuum, said mixture is melted within 15 to 20 minutes at 100° C., homogenized and then introduced into the preheated reactor. The reaction time is 1 hour at 190° C. Polymerization takes place under an inert gas (argon) and accompanied by stirring. The yield is approximately 150 g. The analysis of the raw products gives an inherent viscosity of 1.4 to 1.6 dl/g (HFIP, 30° C.). After comminuting the raw polymer and grinding over a 4 mm screen accompanied by $CO_2$ cooling, the copolymer is purified by extracting several times with ethyl acetate for removing unreacted monomers, oligomers, catalysts and undesired by-products and is then dried for 4 days, at 50° C. in vacuo. The inherent viscosity of the polymer is 1.2 to 1.5 dl/g, and its melting enthalph 30 to 50 J/g.

EXAMPLE 2

Production of glycolide-TMC copolymer with a monomer ratio of 84:16.

For the synthesis of the statistical copolymer 231 g of 1,4-dioxan-2,5-dione and 69 g of 1,3-dioxan-2-one are weighed in under inert conditions (nitrogen) and mixed with 53.3 ppm of tin (as tin octoate in toluene solution) as the catalyst. After removing the toluene in high vacuum, the mixture is melted within 15 to 20 minutes at 100° C., homogenized and then introduced into the preheated reactor (Rheomix kneader of Haake-Buchler). Polymerization takes place at a reaction temperature of 170° C. (max. material temperature 205° C.) over a reaction time of 42 minutes, after which the reaction temperature is increased for 8 minutes to 195° C. The reaction melt is then drained off from the reactor. Polymerization takes place over the entire reaction time under the inert gas argon. The material yields are 235 to 265 g/batch. The raw products have an inherent viscosity of 1.3 to 1.6 dl/g (HFIP, 30° C.). The raw product is ground over a 4 mm screen pack under $CO_2$ cooling and is then dried in vacuo for 3.5 days at 50° C. Purification of the crude polymer with respect to unreacted monomers, oligomerst catalysts and undesired by-products takes place by extraction with ethyl acetate and/or supercritical $CO_2$. The purified copolymer after dried in vacuo at 50° C. for 3 days, is then fractionated over a 1 mm screen pack and packed in air-tight manner whilst excluding moisture. The inherent viscosity of the polymer is 1.3 to 1.6 dl/g, and its melting enthalpy is 40 to 55 J/g.

EXAMPLE 3

Production of glycolide-TMC copolymer with a monomer ratio of 92:8.

For synthesis purposes 261 g of 1,4-dioxan-2,5-dione and 39 g of 1,3-dioxan-2-one are weighed in under inert conditions (nitrogen) and 53.3 ppm of tin (as tin octoate in toluene solution) as the catalyst are mixed therewith. After removing the toluene in high vacuum said mixture is melted for 15 to 20 minutes at 100° C., homogenized and then introduced into the preheated reactor (Rheomix kneader of Haake-Buchler). The polymerization takes place at a reaction temperature of 185° C. (max. material temperature 215° C.) over a reaction time of 37 minutes, after which the reaction temperature is raised to 200° C. for 8 minutes. The reaction melt is then drained off from the reactor. Polymerization takes place over the entire reaction period under the inert gas argon. The yields are 250 to 265 g/batch. The raw products have an inherent viscosity of 1.3 to 1.5 dl/g (HFIP, 30° C.). Processing of the raw product takes place according to example 2. The inherent viscosity of the polymer is 1.2 to 1.5 dl/g and its melting enthalpy is 50 to 65 J/g.

EXAMPLE 4

Production of monofilaments from glycolide-TKC copolymer.

Glycolide-TMC copolymer chips produced according to example 3 and dried for 24 hours, at 50° C. and in high vacuum to a residual moisture content of less than 0.01 wt. %, are fed into a twin-screw extruder. The polymer is melted in the four heating zones at temperatures of 190 to 230° C. Working takes place under the inert gas argon. The screw speed is 10 r.p.m. and the spinning head temperature 190° C. By means of a 1 mm diameter, single-hole spinneret extrusion takes place at 40 bar in a water bath at ambient temperature. The passage length is 120 cm, the passage depth 60 m and the spinneret spacing 10 cm. The coagulated filament is drawn off at ambient temperature and a godet speed of 25 m/min. For producing a surgical sewing thread, the raw thread is stretched in a stretching oven of length 600 cm at 60° C. The speeds of the two stretching godets at ambient temperature are 5 and 35 m/min, so that there is a draw ratio of 1:7. The resulting monofilament is simultaneously thermoset. It has a diameter of 0.19 mm, a knot breaking strength of 17.3 N and a knot extension of 33%.

A comparison of the mechanical characteristics of stretched and thermoset monofilaments produced from the glycolide-TMC copolymers of examples 1 to 3 is given in the following table.

| Glycolide-TMC copolymer | 76:24 | 84:16 | 92:8 |
| --- | --- | --- | --- |
| Copolymer inherent viscosity | 1.4 dl/g | 1.5 dl/g | 1.3 dl/g |
| Monofilament diameter | 0.28 mm | 0.14 mm | 0.19 mm |
| Knot breaking strength | 13.8 N | 8.7 N | 17.3 N |
| Extension | 111% | 38% | 33% |

The monofilament formed from statistical copolymer with 76% glycolide and 24% TMC does not comply with the requirements made on a surgical sewing thread.

EXAMPLE 5

In vitro decomposition of glycolide-TKC copolymer.

For investigating the decomposition behavior of glycolide-TKC copolymer monofilaments produced according to examples 1 to 4, sterilized samples are incubated for 2 weeks at 37° C. in a phosphate buffer at pH 6.1. Before the start of the test and on certain test days samples are taken and tested for their tensile strength. Use is made for this purpose of an INSTRON universal testing machine with a jaw spacing of 10 cm and a transverse yoke speed of 30 cm/min.

The results of the tensile strength tests for a suture material A according to the invention with a glycolide-TMC ratio of 84:1, a suture material B according to the invention with a glycolide-TMC ratio of 92:8 and a suture material C from a commercially available, absorbable multifilament are given in the following table and represented in FIG. 1.

| Sample | A | B | C |
|---|---|---|---|
| Glycolide-TMC ratio | 84:16 | 92:8 | — |
| Incubation time (days) | | | |
| 0 | 565 | 624 | 219 |
| 1 | 553 | 619 | 200 |
| 3 | 541 | 554 | 128 |
| 5 | 487 | 319 | 88 |
| 7 | 410 | 100 | 56 |
| 9 | 262 | 0 | 31 |
| 14 | 30 | 0 | 0 |

EXAMPLE 6

In vivo composition of glycolide-TMC copolymer.

For investigating the decomposition behavior and absorption of glycolide-TMC copolymer monofilaments produced according to examples 1 to 4, ethylene oxide-sterilized thread bundles are introduced into rabbits by subcutaneous implantation. Before the start of the test and on certain test days samples are taken and tested for their tensile strength (not breaking strength). Use is made of an INSTRON universal testing machine with a jaw spacing of 10 cm and a transverse yoke speed of 30 cm/min. The results of the tensile strength tests for a suture material A according to the invention with a glycolide-TMC ratio of 84:16, a suture material B according to the invention with a glycolide-TMC ratio of 92:8 and a suture material C of commercially available, absorbable multifilaments are given in the following table and represented in FIG. 2.

In vivo tensile strength (N/mm$^2$).

| Sample | A | B | C |
|---|---|---|---|
| Glycolide-TMC ratio | 84:16 | 92:8 | — |
| Incubation time (days) | | | |
| 0 | 568 | 571 | 222 |
| 1 | 525 | 533 | 181 |
| 3 | 478 | 454 | 144 |
| 5 | 389 | 205 | 93 |
| 7 | 268 | 30 | 48 |
| 9 | 45 | 0 | 0 |
| 14 | 0 | 0 | 0 |

EXAMPLE 7

Production of monofilaments from glycolide-TeC copolymer with plasticizer content Example 4 is repeated wherein molten oligomer of ε-caprolactone is added to the molten copolymer in a melting zone of a twin-screw extruder. The amount of oligomer was 15 wt. %, based on the total weight of copolymer and oligomer. The extruded monofilaments exhibited improved handling and improved knot properties as comnpared to filaments without plasticizer. The desirable values in breaking strength and degradability were not negatively affected.

We claim:

1. A process for the production of a surgical suture material of an absorbable, synthetic, random copolymer which comprises simultaneously reacting glycolide and trimethylene carbonate monomers to form the random copolymer.

2. Process according to claim 1, characterized in that the copolymer is extruded to a monofilament.

3. Process according to claim 2 wherein the monofilament has a diameter of 0.001 to 0.8 mm, a crystallinity of 15 to 40%, an inherent viscosity of 1 to 2 dg/l, a tensile strength of 250 to 900 N/m$^2$, and an elongation at break of 25 to 45%.

4. Process according to claim 1 wherein the glycolide content of the copolymer is at least 76 wt. % such that the suture material has complete breaking strength loss in vivo within 28 days.

5. Process according to claim 1 wherein a plasticizer is added during formation of the copolymer in an amount sufficient to reduce the elastomeric properties of the suture material.

6. Process according to claim 1 wherein the glycolide content of the copolymer is 80 to 99% by weight, and the suture material retains 50% of its tensile strength after 3 to 10 days and has complete breaking strength loss in vivo within 9 to 21 days.

7. Process according to claim 1 wherein an oligomer of ε-caprolactone is added during formation of the copolymer in an amount sufficient to reduce the elastomeric properties of the suture material.

8. Process according to claim 1 wherein an oligomer of TMC is added during formation of the copolymer.

9. Process according to claim 1 wherein the copolymer is prepared from 1,4-dioxin-2,5-dione and 1,3-dioxin-2-one monomers.

* * * * *